United States Patent
Hsiao

(10) Patent No.: US 12,319,482 B2
(45) Date of Patent: Jun. 3, 2025

(54) PAPER FRAGRANCE CAPSULE WITH BREATHABLE FILM

(71) Applicant: Ming Jen Hsiao, Miaoli County (TW)

(72) Inventor: Ming Jen Hsiao, Miaoli County (TW)

( * ) Notice: Subject to any disclaimer, the term of this patent is extended or adjusted under 35 U.S.C. 154(b) by 65 days.

(21) Appl. No.: 18/355,809

(22) Filed: Jul. 20, 2023

(65) Prior Publication Data

US 2025/0026551 A1  Jan. 23, 2025

(51) Int. Cl.
*B65D 65/42* (2006.01)
*B65D 3/22* (2006.01)
*B65D 43/02* (2006.01)

(52) U.S. Cl.
CPC ............ *B65D 65/42* (2013.01); *B65D 3/22* (2013.01); *B65D 43/0212* (2013.01); *B65D 2543/00092* (2013.01); *B65D 2543/00537* (2013.01); *B65D 2543/0074* (2013.01); *B65D 2543/00796* (2013.01); *B65D 2565/388* (2013.01)

(58) Field of Classification Search
CPC .......... A61L 2209/12; A61L 9/12; A61L 9/03; B65D 65/42; B65D 43/0212; B65D 2543/00092; B65D 2543/00537
USPC ........................................ 220/793
See application file for complete search history.

(56) References Cited

U.S. PATENT DOCUMENTS

| | | | |
|---|---|---|---|
| 4,356,969 A * | 11/1982 | Obermayer | A01M 1/2044 239/6 |
| 4,781,895 A | 11/1988 | Spector | |
| 4,849,606 A * | 7/1989 | Martens, III | B65D 77/2024 239/34 |
| 5,395,047 A * | 3/1995 | Pendergrass, Jr. | A61L 9/12 428/905 |
| 5,439,100 A * | 8/1995 | Gordon | A61L 9/12 261/DIG. 89 |
| 6,085,026 A | 7/2000 | Hammons et al. | |
| 6,413,476 B1 | 7/2002 | Barnhart | |
| 8,668,885 B2 | 3/2014 | Wirz | |
| 8,765,073 B1 | 7/2014 | Hsiao | |
| 8,787,739 B2 | 7/2014 | Hsiao | |
| 8,938,159 B2 | 1/2015 | Hsiao | |

(Continued)

FOREIGN PATENT DOCUMENTS

| AU | 2012101327 A4 | 1/2013 |
|---|---|---|
| CN | 201055531 Y | 5/2008 |

(Continued)

*Primary Examiner* — Ernesto A Grano
(74) *Attorney, Agent, or Firm* — Sinorica International Patent & Trademark

(57) ABSTRACT

A paper fragrance capsule with breathable film, includes a paper container, a fragrance carrier filled with a fragrance substance and placed in the paper container, a breathable film peripherally combined with an opening extension of the paper container and a paper sealing cover combined with the opening extension and covering the paper container. The breathable film is formed by combing a microporous film with a tensile fixing layer, which can fix the heated microporous film and limiting the deformation of the microporous film. When using the fragrance capsule, you can remove the paper sealing cover smoothly first, and then place the fragrance capsule in the aroma diffuser to heat to generate aroma. After use, the paper fragrance capsule can be discarded and decomposed or recycled. It is more environmentally friendly to use.

12 Claims, 8 Drawing Sheets

(56) References Cited

U.S. PATENT DOCUMENTS

| | | | |
|---|---|---|---|
| 8,974,107 B2 | 3/2015 | Hsiao | |
| 8,983,277 B2 | 3/2015 | Hsiao | |
| 9,028,759 B2 | 5/2015 | Wirz | |
| 9,031,392 B2 | 5/2015 | Hsiao | |
| 9,109,780 B2 | 8/2015 | Hsiao | |
| 9,206,963 B2 | 12/2015 | Hsiao | |
| 9,410,695 B2 | 8/2016 | Hsiao | |
| 9,498,553 B2 | 11/2016 | Hsiao et al. | |
| 9,500,358 B2 | 11/2016 | Hsiao | |
| 9,849,206 B1* | 12/2017 | Hsiao | A61L 9/127 |
| 2006/0175327 A1* | 8/2006 | Kirkland | B65D 77/2076 |
| | | | 220/4.21 |
| 2011/0110824 A1 | 5/2011 | Hsiao | |
| 2012/0020052 A1 | 1/2012 | McCavit | |
| 2014/0072286 A1 | 3/2014 | Hsiao | |
| 2014/0110389 A1 | 4/2014 | Hsiao | |
| 2014/0166774 A1* | 6/2014 | Morhain | A61L 9/12 |
| | | | 239/34 |
| 2015/0109823 A1 | 4/2015 | Hsiao | |
| 2015/0117056 A1 | 4/2015 | Hsiao | |
| 2015/0314028 A1* | 11/2015 | Hsiao | A61L 2/00 |
| | | | 362/96 |
| 2015/0374871 A1 | 12/2015 | Cew | |
| 2016/0195257 A1* | 7/2016 | Hsiao | F21V 33/0004 |
| | | | 362/92 |
| 2016/0325002 A1* | 11/2016 | Hsiao | A61L 9/14 |
| 2016/0375168 A1* | 12/2016 | Hsiao | A61L 9/03 |
| | | | 392/390 |
| 2016/0375169 A1* | 12/2016 | Hsiao | F21V 33/0028 |
| | | | 362/92 |
| 2017/0128608 A1* | 5/2017 | Hsiao | A61L 9/12 |
| 2018/0064839 A1* | 3/2018 | Hsiao | A61L 9/03 |
| 2019/0022267 A1* | 1/2019 | Hsiao | A61L 9/03 |
| 2021/0127869 A1* | 5/2021 | Le | A47G 19/03 |
| 2023/0364879 A1* | 11/2023 | Ji | B31B 50/006 |

FOREIGN PATENT DOCUMENTS

| | | |
|---|---|---|
| EP | 0321729 A2 | 6/1989 |
| EP | 1473046 A1 | 11/2004 |
| EP | 1627647 | 2/2006 |
| EP | 2067491 A1 | 6/2009 |
| EP | 2679249 A1 | 1/2014 |
| JP | 2004057452 A | 2/2004 |
| WO | 2003089018 A1 | 10/2003 |

* cited by examiner

PAPER FRAGRANCE CAPSULE WITH BREATHABLE FILM

BACKGROUND OF THE INVENTION

1. Field of the Invention

The invention relates to a fragrance capsule used for heating in an aroma diffuser and more particularly, to a paper fragrance capsule with a breathable film.

2. Description of the Related Art

The container of the fragrance capsule in the inventor's existing patents such as US20180064839A1, U.S. Pat. Nos. 8,668,885, 9,550,358, 9,498,553, EP Pat. No. 2679249, is mainly made of plastic or metal, and it is disposable and not environmentally friendly.

The existing liquid fragrances of different properties or containers filled with solid scented wax are used for heating and melting by aromatherapy heaters, and users must use them carefully to avoid the liquid fragrance falling from the container or flowing out into the heater and the environment, causing contamination or danger. In particular, even if the liquid aromatic substances or volatile fragrances are filled in the fragrance capsules, the fragrances may stick and block the breathable film of the capsules, which may affect the efficiency of the aromatic vapor passing through the breathable film.

In some embodiments, the heater heats the fragrance capsule, and the aromatic hot steam generated by the internal fragrance increases the pressure inside the fragrance capsule, and the breathable film will expand. When the aromatherapy heating machine stops heating the fragrance capsule, the expanded breathable film may also cool down and shrink and wrinkle, thereby affecting the performance of the fragrance capsule in releasing aromatic gas.

The fragrance in the US20180064839A1 fragrance capsule may be volatile. The opening extension of the container is closed by the sealing cover, so as to maintain the fragrance of the fragrance substance in the fragrance capsule without volatilization during long-term transportation or storage. The paper sealing cover is not easy to open with fingers, especially when opened with one hand.

SUMMARY OF THE INVENTION

In order to overcome or at least improve the above problems, the present invention provides a paper fragrance capsule with a breathable film, which is easy to decompose or recycle, and is more environmentally friendly.

The invention also provides a paper fragrance capsule with a breathable film to be heated in an aroma diffuser, the breathable film is not easy to expand and deform, does not affect the pore exhaust of the breathable film, and maintains a good efficiency of releasing aromatic gas.

The present invention also provides a paper fragrance capsule with a breathable film, wherein the fragrance substance is combined in a fragrance carrier with pores, and then filled into the paper fragrance capsule with a breathable film, and the liquid fragrance substance can avoid or reduce contact with air and the breathable film during transportation or use, without affecting the breathable effect of the breathable film, and the fragrance substance is less likely to be volatilized and lost in the capsule.

The paper fragrance capsule with breathable film of the present invention can replace or reduce the environmental unfriendly problems of using plastic containers for fragrances, and the paper fragrance capsules can be recycled and reused after being heated by the aromatherapy machine, or the degradable environmentally friendly paper fragrance capsule can be buried in the soil to decompose without affecting the environment.

The present invention is a paper fragrance capsule with breathable film, comprising: a paper container, a fragrance carrier, and a breathable film. The paper container comprises an opening extension, and a first coating coated on an inner side of the paper container and the opening extension. The fragrance carrier is placed in the paper container, comprising a plurality of third pores filled with a fragrance substance inside. The breathable film is waterproof and breathable and covered on the fragrance carrier with the peripheral edge thereof combined with the opening extension. The breathable film comprises a tensile fixing layer and a microporous film. The tensile fixing layer comprises a plurality of first pores. The microporous film comprises a plurality of second pores. The tensile fixing layer combines with the microporous film to form the breathable film. The pore diameter of the first pores is larger than the pore diameter of the second pores, so as to facilitate the permeation of gas. The paper fragrance capsule is used to be placed in an aroma diffuser and heated to quickly generate aroma, which is released from the first pores and second pores to diffuse into the space. Using the microporous film of this layer (such as thermoplastic elastomer TPE) and its second pores can achieve waterproof and moisture-permeable effect, and also maintain the fragrance substance inside the paper fragrance capsule in storage.

The first coating includes any one of PE, PP, PLA or CPE, etc. The most common plastic coatings are PET, LDPE, HDPE, LLDPE or Propylene ethylene, etc. Because paper is generally not waterproof, the first coating is coated on the inside of the paper container and the opening extension by various methods such as coating or bonding to prevent the oil and water of the liquid fragrance substance or melted solid fragrance substance in the paper fragrance capsule from penetrating into the paper container.

Compared with plastic containers, the recycling of plastic-coated paper container fragrance capsules is mainly based on paper, and plastic only accounts for a very small proportion of a layer of film, so the risk of exposure to plastic toxins is relatively low. At the same time, the present invention can use recycled environmentally friendly paper materials, reducing pollution and being more friendly to the environment.

In the paper fragrance capsule with breathable film of the present invention, the fragrance substance is combined in the fragrance carrier, such as a porous material or absorber, and then filled into the paper fragrance capsule with breathable film. Liquid fragrance substance or aromatic wax is melted and filled in the porous fragrance carrier during transportation or use, which can avoid or reduce contact with air and the breathable film, without affecting the breathable effect of the breathable film. The paper fragrance capsule with breathable film can keep the fragrance substance less volatilized in the capsule, and has good aroma vapor release efficiency when heated by a heater.

When the aroma diffuser heats the fragrance capsule, the microporous film of the breathable film expands or shrinks and shrinks when cooled. Since the microporous film is divided into multiple regions by the tensile fixing layer of the mesh structure film, the thermal expansion and deformation of the microporous film will be blocked by the tensile fixing layer to a certain extent, and its small deformation is also localized, which affects the gas emission of aromatics to a limited extent.

Using the tensile fixing layer as the tensile material of the breathable microporous film, the expansion tension or shrinkage tension generated by the microporous film has been limited by the tensile fixing layer, and the breathable film can maintain a good ventilation effect.

The paper fragrance capsule with breathable film further comprises a paper sealing cover. The paper sealing cover of the fragrance capsule can be opened with one hand, which is convenient for use in the aroma diffuser.

DETAILED DESCRIPTION OF THE PREFERRED EMBODIMENT

Figure 1:
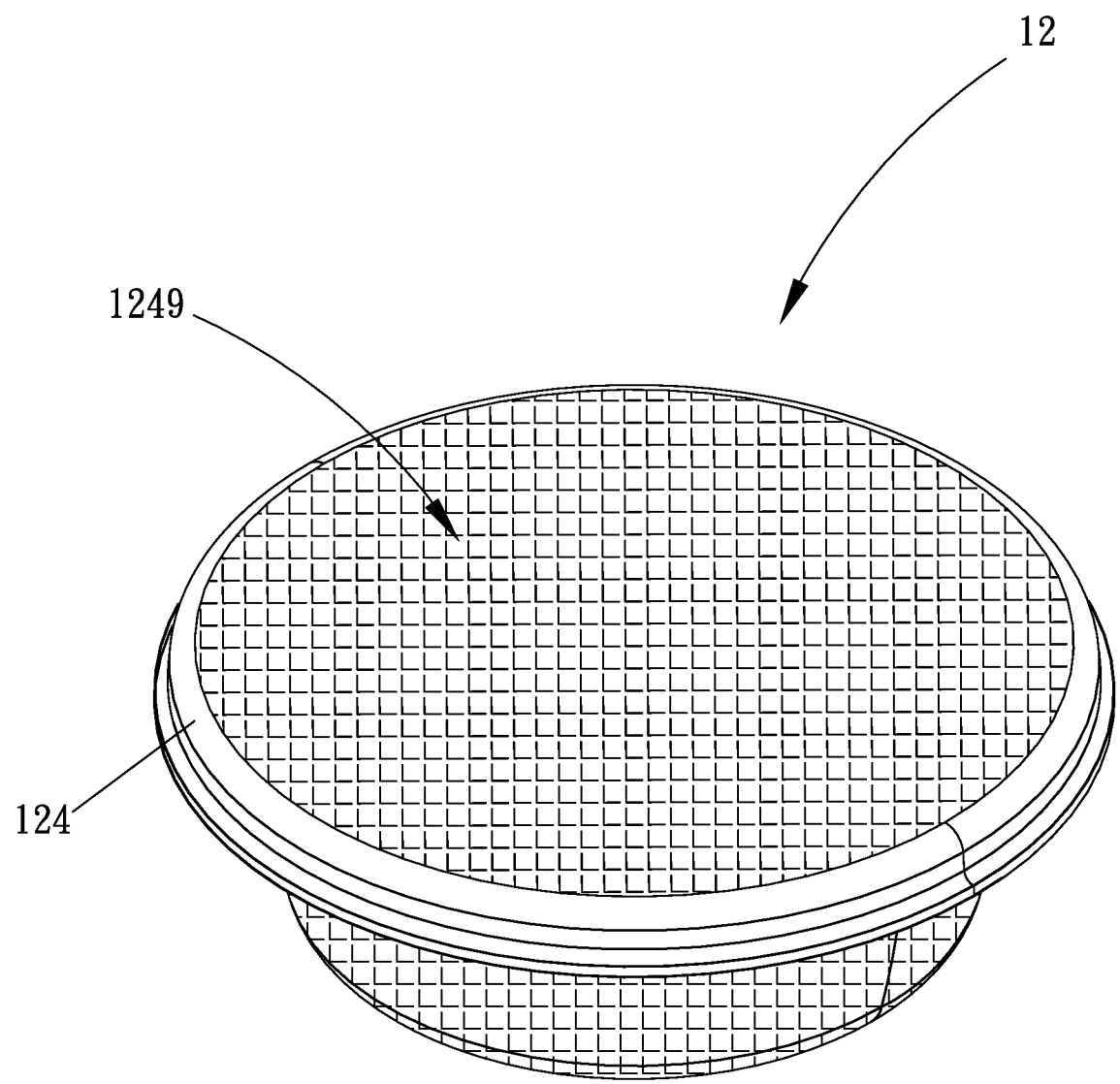
FIG. 1 is a perspective view of the appearance of an embodiment of a paper fragrance capsule with a breathable film according to the present invention.
Figure 2:
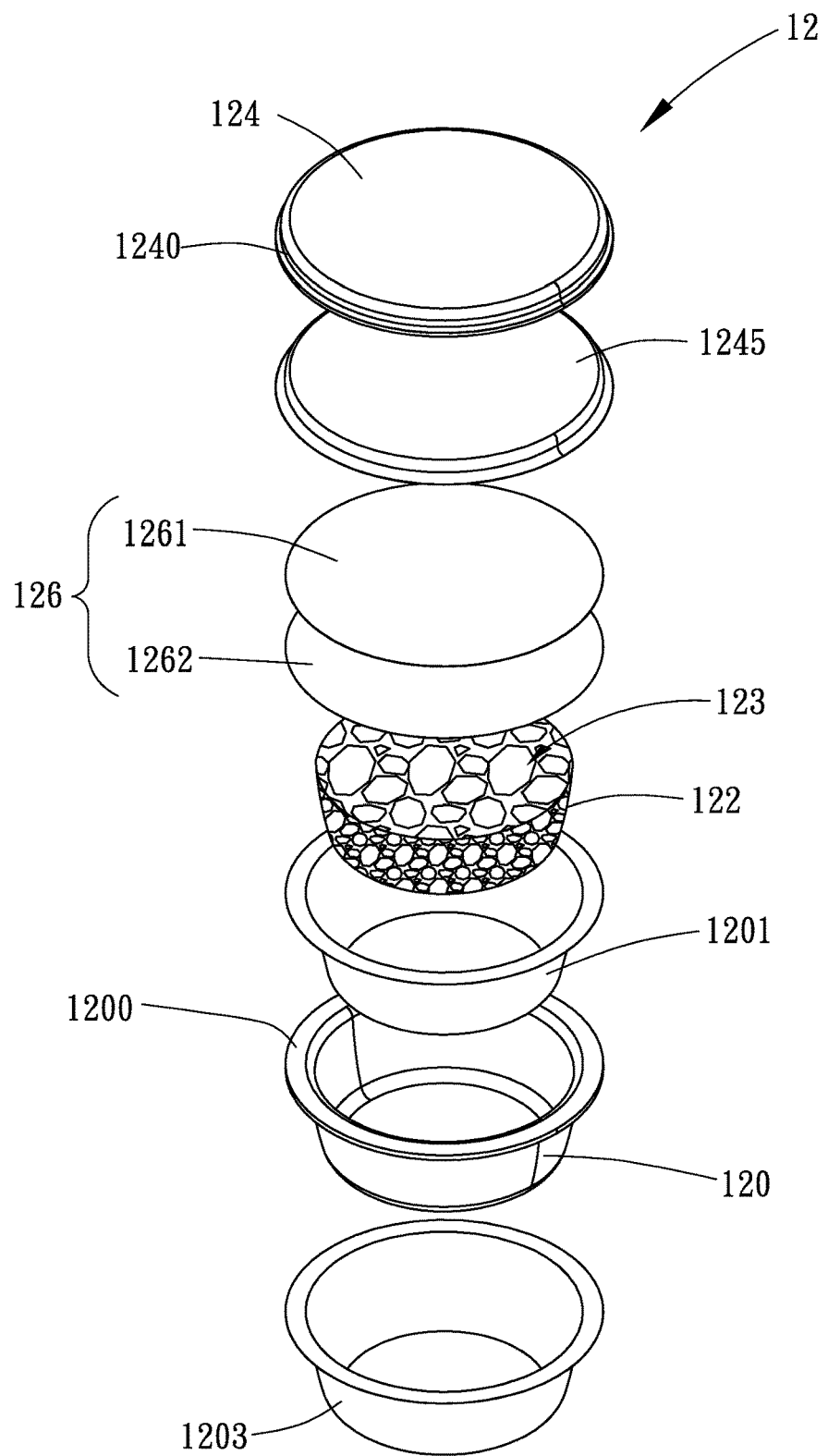
FIG. 2 is an exploded view of the paper fragrance capsule with breathable film of the present invention.
Figure 3:
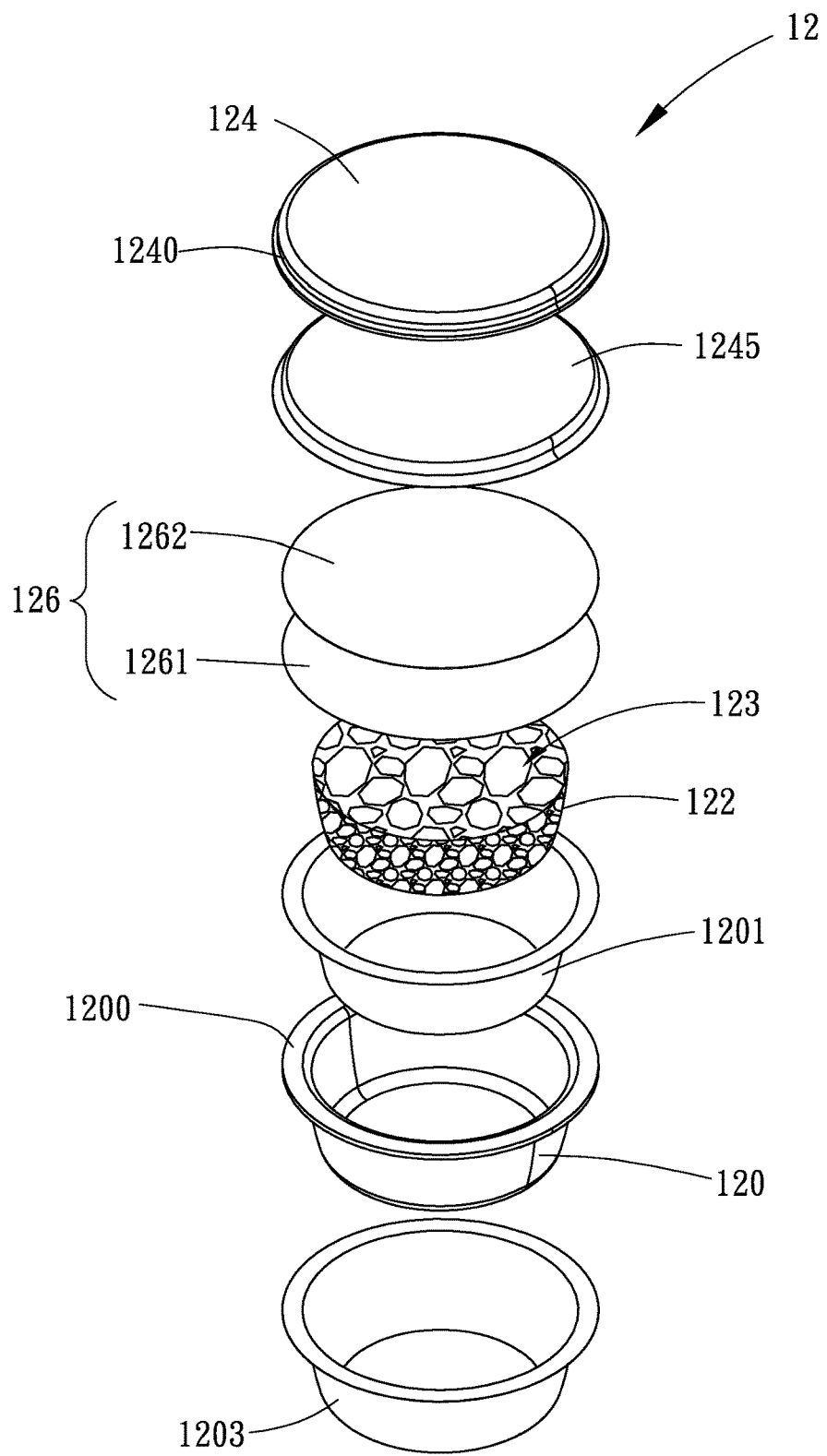
FIG. 3 is an exploded view of another embodiment of the paper fragrance capsule with breathable film of the present invention.

Referring to FIGS. 1, 2 and 3, a paper fragrance capsule with a breathable film in the present invention comprises: a paper container 120, a fragrance carrier 122, and a breathable film 126. The paper container 120 comprises an opening extension 1200, and a first coating 1201 bonded to the inner side of the paper container 120 and the opening extension 1200. The fragrance carrier 122 has third pores 123 filled with a fragrance substance inside. The breathable film 126 comprises a tensile fixing layer 1261 and a microporous film 1262. The tensile fixing layer 1261 has first pores 1263. The microporous film 1262 has second pores 1264. The tensile fixing layer 1261 is combined with the microporous film 1262 to form the breathable film 126. The pore diameter of the first pores 1263 is larger than that of the second pores 1264. The fragrance carrier 122 is placed in the paper container 120. The peripheral portion of the breathable film 126 is combined with the opening extension 1200 and covers the fragrance carrier 122. The breathable film 126 has waterproof and breathable function. The paper fragrance capsule 12 is used to be placed in an aroma diffuser (not shown in the figures) and heated to quickly generate aroma, which is released from the first pores 1263 and second pores 1264 to diffuse into the space.

The ventilation aperture of the first pores 1263 may be larger than the ventilation aperture of the second pores 1264, of the so as to facilitate the permeation of gas. Using the microporous film 1262 (such as thermoplastic elastomer TPE) and its second pores 1264 in this layer can achieve waterproof and moisture-permeable effects, and also maintain the fragrance inside the paper fragrance capsule 12 in storage. Applicant's former application the Replaceable multilayer breathing film-based aroma capsule and aroma-diffusing heating device using same, US 20180064839A1 which is incorporated herein in its entirety.

The first coating 1201 includes any one of PE, PP, PLA or CPE, etc. The most common plastic coatings are PET, LDPE, HDPE, LLDPE or Propylene ethylene, etc. Because paper is generally not waterproof, the first coating 1201 is bonded on the inner side of the paper container 120 and the opening extension 1200 by various methods such as coating or bonding, so as to prevent the liquid fragrance in the paper fragrance capsule 12 or the oil and water of the melted solid fragrance from penetrating into the paper container 120.

Compared with plastic and other containers, the recycling of plastic-coated paper container fragrance capsules is mainly based on paper, and plastic only accounts for a very small proportion of a layer of film, so the risk of exposure to plastic toxins is relatively low. At the same time, the present invention can use recycled environmentally friendly paper materials, reducing pollution and being more friendly to the environment. In some embodiments, for example, LDPE, PET, PE or some ultra-high molecular weight polyethylene porous films are used as the first coating 1201, which does not completely block the air itself. The pores of these plastic films are smaller than the particles of water molecules, but larger than the pores of gas molecules. The fragrance substance in the fragrance carrier 122 in the paper fragrance capsule 12 of the present invention generates aromatic steam and hot air pressure when heated. The aromatic vapor can be released from the pores of the first coating 1201 and the paper container 120, and the heat and internal pressure in the paper fragrance capsule 12 are reduced, which helps to reduce the expansion and deformation of the microporous film 1262.

Figure 4:
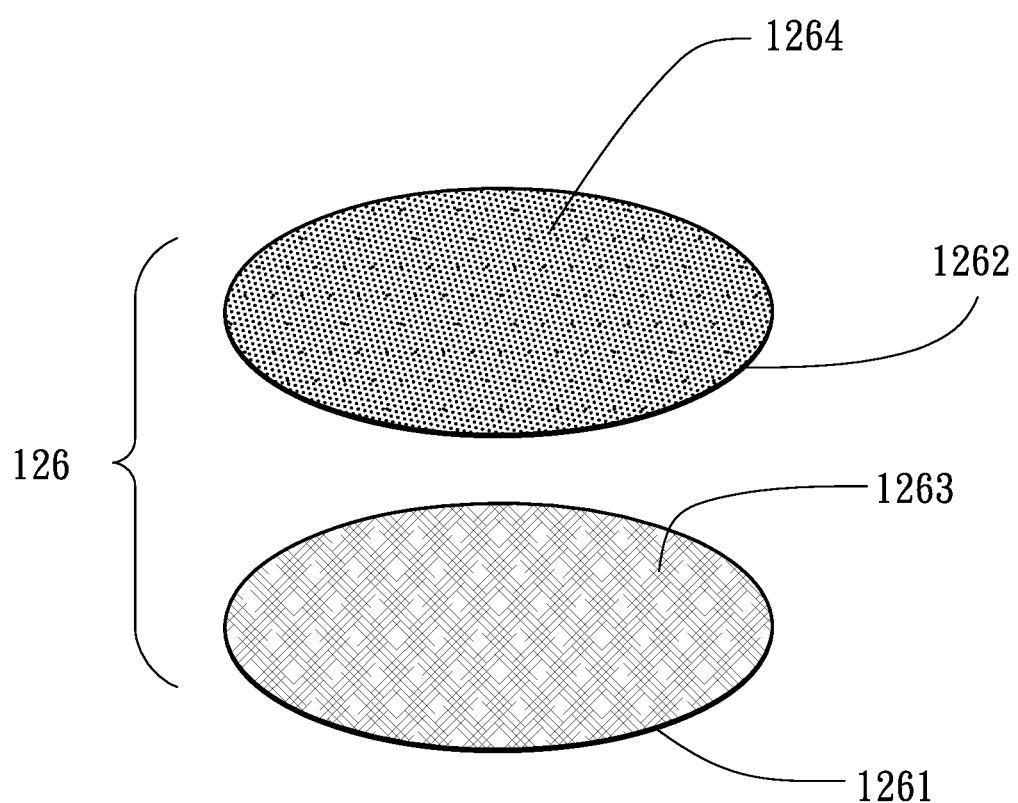
FIG. 4 is an exploded view of the composition of the breathable film of the paper fragrance capsule with the breathable film of the present invention.
Figure 5:
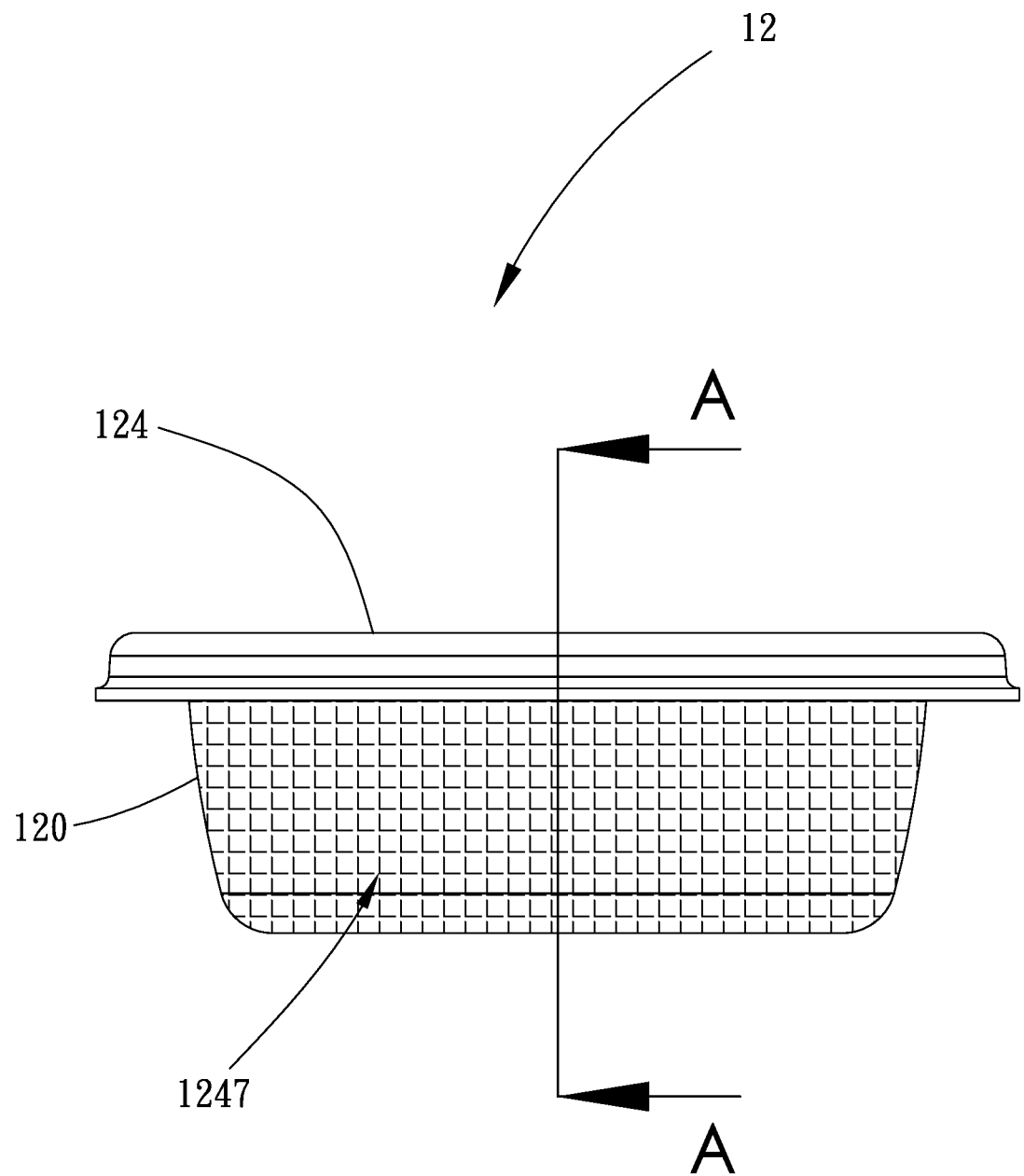
FIG. 5 is a schematic view of the side appearance of the paper fragrance capsule with breathable film in the present invention.

Please refer to FIG. 2, FIG. 3 and FIG. 4, in an embodiment of the present invention, the microporous film 1262 of the paper fragrance capsule with breathable film is mainly waterproof and moisture-permeable, it only allows gas or steam holes to pass through, and blocks water molecules from passing through, and its material includes thermoplastic elastomer TPE, TPU, PE, polytetrafluoroethylene (PTFE), polyolefin, PU or precipitated polyurethane; The tensile fixing layer 1261 is a mesh structure film, which bonds a tensile material in a network-like elongated film on one side of the microporous film 1262, so that the tensile fixing layer 1261 forming the mesh structure film serves as the fixed skeleton of the microporous film 1262. The microporous film 1262 expands when heated and contracts when cooled. The tensile fixing layer 1261 acts as a tensile material to support the microporous film 1262 without deformation, and the second pores 1264 can maintain good air permeability.

As for the paper fragrance capsule with breathable film, the tensile fixing layer 1261 material formed by the mesh structure film includes any one of tensile materials such as fiber, carbon fiber, glass fiber, polyester fiber, nylon, PP, plastic or metal. Compared with microporous film 1262, these tensile materials have better chemical resistance, less thermal deformation at higher temperatures, high toughness and low ductility.

The mesh structure film of the tensile fixing layer 1261 may be a regular or irregular mesh. The meshes divide the microporous film 1262 into a plurality of regions, and the plurality of regions of these intervals are corresponding to the regions of the microporous film 1262 surrounded by the first pores 1263. The aforementioned microporous film 1262 is divided into a plurality of regions by the mesh structure film of the tensile fixing layer 1261. When the microporous film 1262 is thermally expanded and deformed to a certain extent, it will be limited by the tensile material of the tensile fixing layer 1261, and its micro-deformation is also localized, which affects the gas distribution of aromatics to a limited extent, so that the breathable film 126 maintains a certain degree of good exhaust effect.

Please refer to FIGS. 2-5, in an embodiment of the present invention, the material of the microporous film 1262 of the paper fragrance capsule with breathable film includes thermoplastic elastomer TPE, TPU, PE, polytetrafluoroethylene (PTFE), polyolefin, PU or precipitated polyurethane; The tensile fixing layer 1261 is a fiber fixation layer containing fiber cloth, polyester fiber cloth, TETORON™ cloth, PET cloth or non-woven cloth, etc. The tensile fixing layer 1261 of the fiber cloth of the porous fabric has at least two layers of fibers interweaved randomly and laminated to form the plurality of fine first pores.

The tensile fixing layer 1261 of the fiber fixation layer divides the microporous film 1262 into multiple regions. Although the microporous film 1262 has poor heat resistance, the fiber fixation layer separates the microporous film 1262 into many regions and acts as a tensile material. The microporous film 1262 expands or shrinks when the paper fragrance capsule 12 is heated to produce aromatic vapor and pressure, and the deformation will be limited by the tensile fixing layer 1261 to a certain extent. The small deformation is also localized in these spaced regions, without affecting other parts of the microporous film 1262, and can maintain the efficient release of the aromatic gas from the breathable film 126.

Please refer to FIG. 2 to FIG. 7, in an embodiment of the paper fragrance capsule with breathable film of the present invention, the periphery of the breathable film 126 is bonded to the first coating 1201 of the opening extension 1200. The first coating 1202 and the breathable film 126 are both made of plastic film. The paper container 120 and the plastic breathable film 126 can be bonded in a dot-matrix distribution manner using glue or adhesive, or thermocompression fusion or high-frequency bonding can be used to solve the problem of combining the paper container 120 and the plastic breathable film 126.

The base fiber material of the fiber fixation layer can be organic or inorganic fibers, such as polymeric fibers, chemical fibers, polyester, cellulose, rayon, glass fibers, and carbon fibers. Alternatively, natural fibers such as plant fibers, wood fibers, silk, and paper fibers can be selectively used. The base fiber material is a porous thin film, fabric or nonwoven fabric in a predetermined shape and size, having a certain degree of heat resistance.

During the fabrication of the fiber fixation layer, the aperture of the first pores of the fiber fixation layer can be controlled by means of the control of the fiber tightness of the matrix material. Pore forming agent can also be used in the fabrication of the fiber fixation layer to form the desired first pores.

The microporous layer has a waterproof and moisture permeable function. The microporous layer is a multi-(micro) hole matrix material, or a microporous film or fabric made of a matrix material (such as polymer) with the application of a hole forming agent (gas or filler). The microporous layer defines therein a plurality of second pores. During the fabrication of the microporous layer, multiple micro pores are formed therein subject to the use of a hole forming agent. McCormark WO 96/19346 discloses methods of making breathable microporous films having zoned breathability.

In some embodiments of the present invention, the microporous layer is selected from, but not limited to, films made using, for example, thermoplastic elastomer (TPE) compositions, which are prepared by melt-plasticizing the film, or by, for example, stretching the film to create micro pores. Filler particles or hole forming agent can be selectively used for making the microporous layer to create the desires micro holes. The applied filler material, oil or hole forming agent is mixed with the thermoplastic elastomer (TPE). Forming, solution film forming, stretching, electrostatic spinning and direct drilling techniques can be selectively used for making a thin film with μm grade micro pores of size even below 10 μm. Precision instrument or etching technique can be employed for the creation of the desired micro pores. The use of a thermoplastic elastomer (TPE) film without pores can simply selectively allow gas to pass. The open space of each of the second pores allows the released aromatic vapor molecules to pass therethrough. The choice of microporous layer with moisture permeability and good masking properties can block melted aromatic substance or spices fluid, prohibiting melted aroma wax or essential oil from passing therethrough. The second pores of the microporous layer provide waterproof and moisture permeable effects. The microporous layer and the fiber fixation layer are bonded together to create the desired breathing film that is then bonded to the heat-transfer container over the top opening to block the melted aromatic substance from falling to the outside of the aroma capsule.

In one embodiment of the present invention, the thermoplastic elastomer (TPE) microporous layer defines therein a plurality of second pores. the thermoplastic elastomer (TPE) is thermoplastic urethane (TPU); the fiber fixation layer is TETORON™ or polyethylene terephthalate (PET). TETORON™ is formed by the condensation of terephthalic acid and ethylene glycol linear polymer. The fabric made out of polyethylene terephthalate is called as Dacron that is hot pressed to create the fiber fixation layer. Glass fiber can be added to polyethylene terephthalate to enhance stiffness and heat resistance with the first pores defined therein. Polyester products such as polyester fabric or nonwoven fabric can be used as a substitute. Silk cloth can also be selectively used for the fiber fixation layer; the thermoplastic elastomer (TPE) includes TPU, TPR, TPV, TPEE, TPO or TPA.

In an embodiment, the paper fragrance capsule 12 of the present invention is heated in an aroma diffuser, usually at a temperature below 90 degrees Celsius or lower, such as 70 degrees or 80 degrees, and the fragrance carrier 122 can generate gas molecules and release fragrance. These temperatures will not affect the size of the tensile fixing layer 1261, and the tensile fixing layer 1261 can be used as a tensile material for the expansion and contraction of the microporous film 1262 to support the microporous film 1262 without deformation and maintain the breathability of the second pores 1264.

Figure 6:
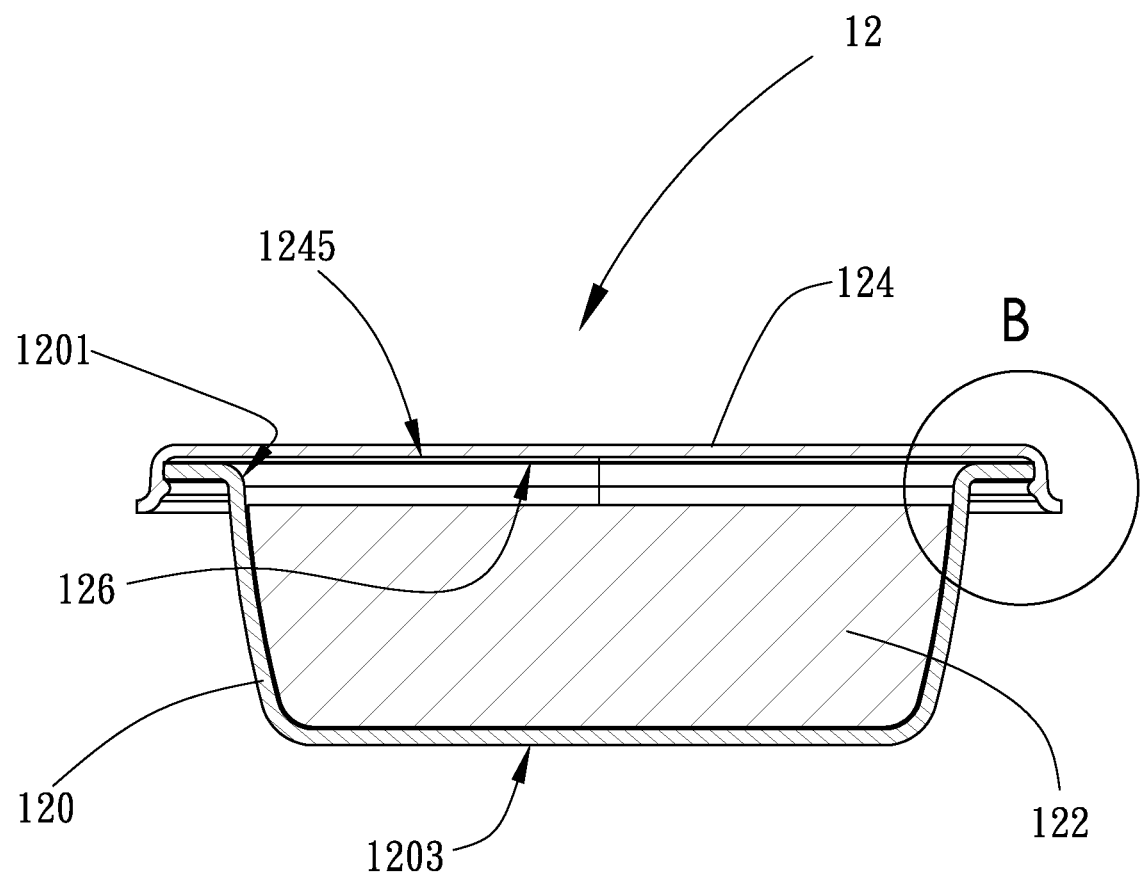
FIG. 6 is the A-A section view of FIG. 5.

Please refer to FIG. 2, FIG. 3 and FIG. 6, in one embodiment of the present invention, the material of the fragrance carrier 122 includes any one of absorber, sponge, foam, open-pore sponge, porous ceramics, gypsum, wood, cloth, fiber cloth, paper or porous rubber. The fragrance substance of the fragrance carrier 122 includes, for example, any one of liquid essential oils, scented waxes, spices, balsams, scented oils and fragrance mixtures, or essential oils, and the scents or scented oils can be absorbed by the absorbent materials of the above-mentioned fragrance carrier 122 into the pores for storage, not easy to flow or volatilize. Compared with the conventional fragrance capsules, the liquid fragrance inside the fragrance carrier 122 will not touch the breathable film during the movement, and the second pores 1264 of the microporous film 1262 can maintain an effective air permeability. In some embodiments, the paper fragrance capsule 12 uses scented wax, which only needs to be heated and melted into a liquid, so as to be absorbed by the absorbent materials of the aforementioned fragrance carrier 122 and stored inside the pores. As long as the aroma diffuser heats the paper fragrance capsule 12 to about 70 degrees, the scented wax can be melted to produce aroma molecules, and the aroma diffuses out through the breathable film 126 in the environment. Compared with existing products, the breathable film 126 of the present invention will not be deformed and ugly during the heating process, and the efficiency of aroma molecules passing through the breathable film 126 is better. In this way, the fragrance substance will not disappear and dissipate in a short time, and the paper fragrance capsule 12 can be used for a longer period of time.

Figure 7:
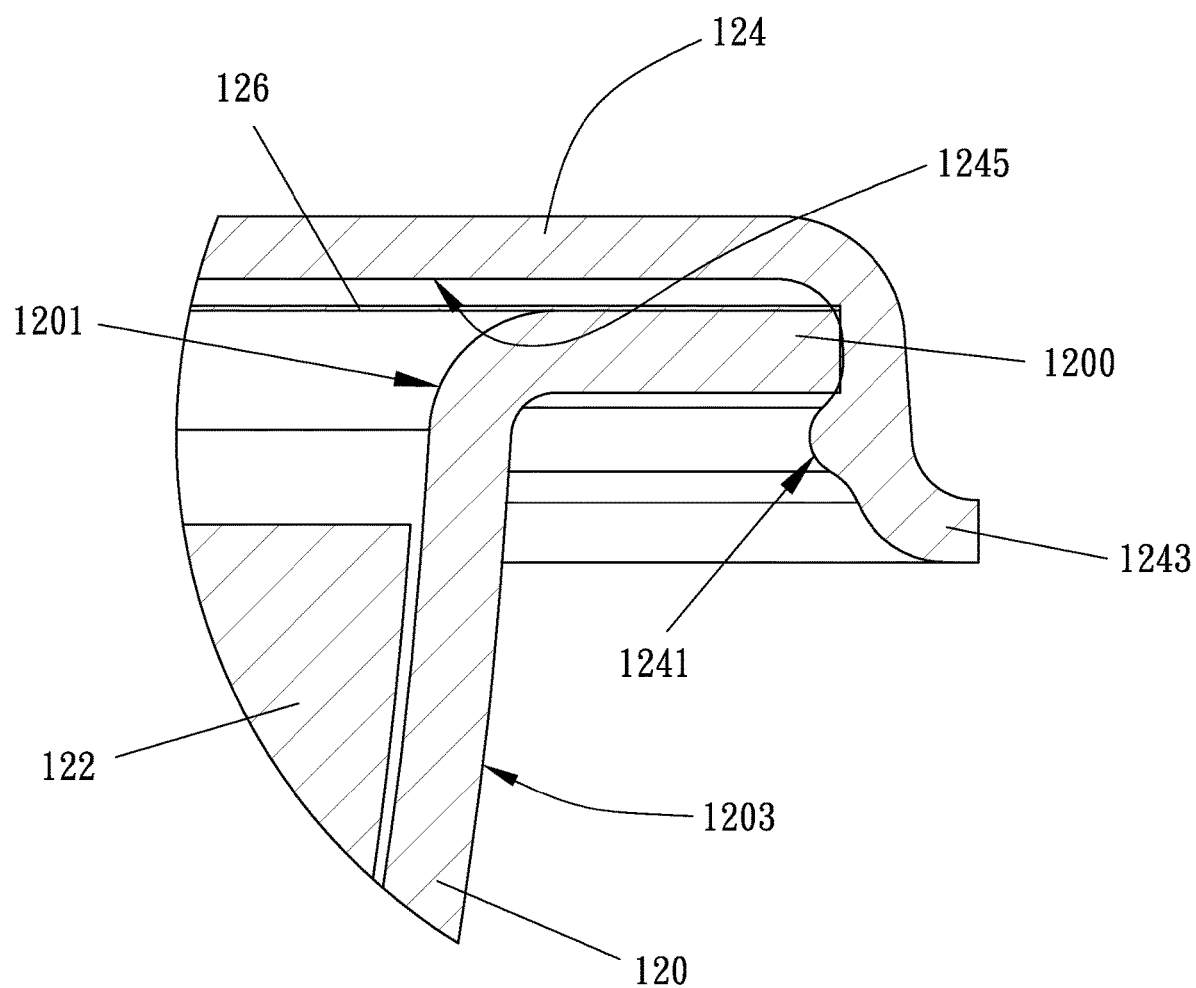
FIG. 7 is a partially enlarged cross-sectional view of Part B in FIG. 6.

Please refer to FIG. 1 and FIG. 7, in one embodiment of the present invention, the material of the paper container 120 includes any one of industrial paper, stationery paper or food paper. For example, coated paper with PLA coating, white cardboard with high hardness, smooth coated paper, yellow kraft paper with strong toughness or packaging cardboard, preferably such as environmentally friendly recycled paper, etc. can all be used in the paper fragrance capsule 12 of the present invention. The paper container 120 will not melt or deform within the above heating temperature, and can conduct the heat energy generated by the aroma diffuser after electrification to the fragrance carrier 122. In a preferred embodiment, the paper container 120 is made of coated paper or environmentally friendly recycled paper. It has the function of heat conduction to conduct heat to the fragrance carrier 122 to emit fragrance. Moreover, the paper container 120 is ductile, tough and not easy to break, can be heated without damage and can transmit heat source to the fragrance substance, and it is easy to recycle and environmentally friendly, which is different from the existing plastic containers that are not environmentally friendly and ceramic bowls and glass containers that are fragile.

Please refer to FIG. 2 and FIG. 6, in one embodiment of the present invention, the upper side of the microporous film 1262 is combined with the tensile fixing layer 1261, and the peripheral edge of the microporous film 1262 is combined with the first coating 1201 of the opening extension 1200 of the paper container 120, so that the peripheral edge of the microporous film 1262 can be firmly fixed and will not easy to fall off.

Please refer to FIG. 3, FIG. 4 and FIG. 6, in one embodiment of the above-mentioned paper fragrance capsule with breathable film of the present invention, the lower side of the microporous film 1262 is combined with the tensile fixing layer 1261, and the peripheral edge of the microporous film 1262 is combined with the first coating 1201 of the opening extension 1200 of the paper container 120. The fragrance substance (such as scented wax or perfume or essential oil) in the fragrance carrier 122 is heated to produce aroma molecules, which pass through the first pores 1263 of the fiber-fixed film 1261 and then pass through the second pores 1264 of the microporous film 1262 to the external environment.

The peripheral edge of the tensile fixing layer 1261 is fixed on the opening extension 1200 of the paper container 120, and at the same time, the part of the microporous film 1262 in the meshes of the peripheral edge of the tensile fixing layer 1261 is fixed on the opening extension 1200 of the paper container 120 along with the peripheral edge of the tensile fixing layer 1261. When the microporous film 1262 is heated and expands and then cools and contracts, the traction fixed on the opening extension 1200 can be further used to further resist the tensile force of the expansion or contraction of the microporous film 1262, thereby limiting deformation and further maintaining better breathable effect of the second pores 1264.

Please refer to FIG. 2, FIG. 6 and FIG. 7, in one embodiment of the present invention, the inner side of the paper sealing cover, referenced by 124, is combined with a layer of second coating 1245. The second coating 1245 is used to further enhance the sealing performance of the paper sealing cover 124, and at the same time, the second coating 1245 increases the toughness of the paper sealing cover 124, and the paper sealing cover 124 is less likely to be broken and damaged.

Figure 8:
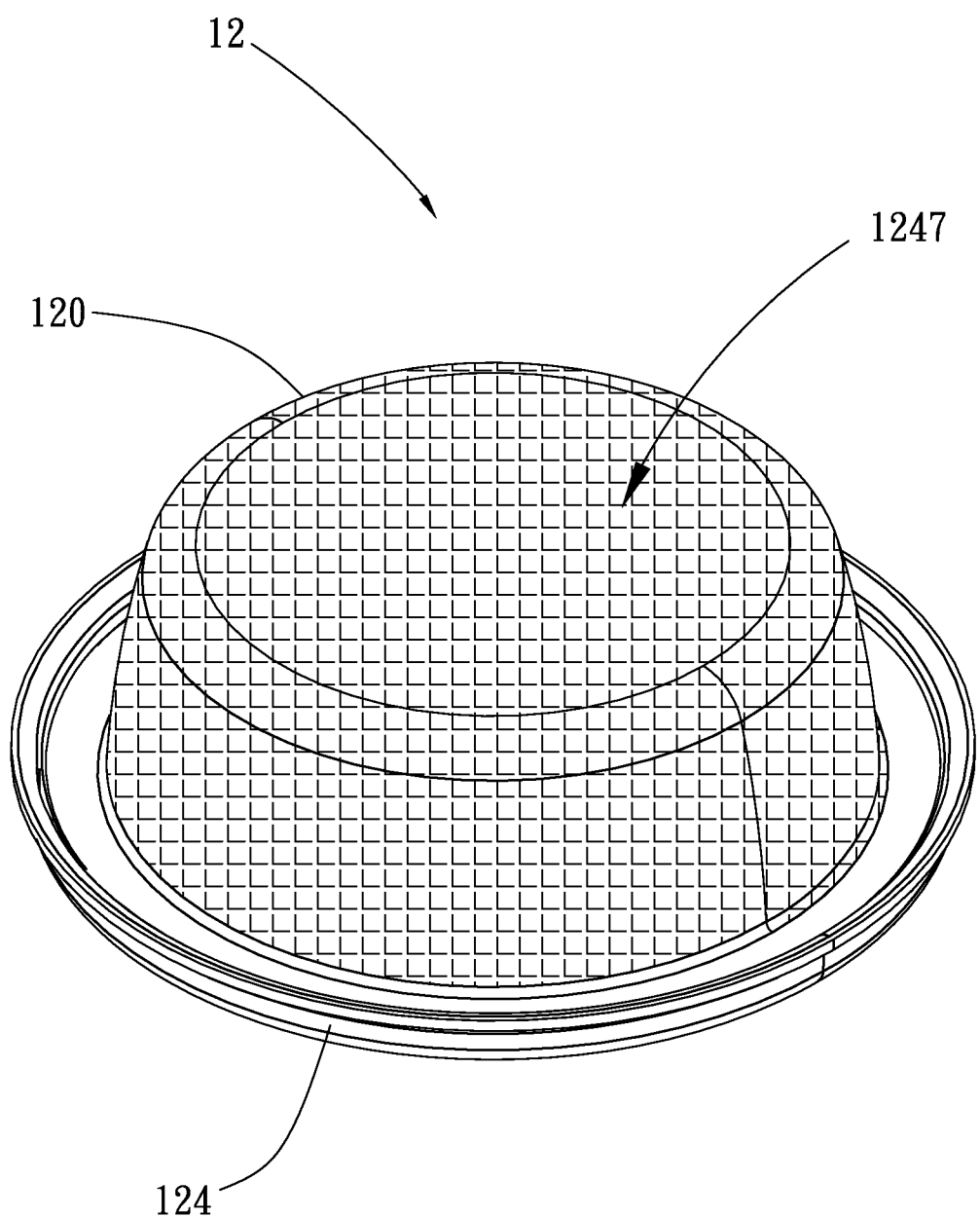
FIG. 8 is another perspective view of the appearance of the embodiment of the paper fragrance capsule with breathable film of the present invention.

Please refer to FIG. 1 and FIG. 8, in one embodiment of the present invention, the paper container 120 or/and the paper sealing cover 124 is formed with a paper sealing cover coefficient surface 1247 with a rough surface. The paper sealing cover coefficient surface 1247 enhances the rigidity of the paper fragrance capsule 122, so that the thinner paper container can increase the loading weight and support the compression resistance, and the paper sealing cover 124 is less likely to be deformed.

Please refer to FIG. 6, FIG. 7 and FIG. 8, in one embodiment of the present invention, the paper sealing cover 124 has a cover eaves 1240 extending downwards from the periphery, an inner locking protrusion 1241 located on an inner side of the cover eaves 1240, and a pluck end 1243 protruding outward from the inner locking protrusion 1241. The paper sealing cover 124 is incorporated with the opening extension 1202. The inner locking protrusion 1241 is used to releasably engage with the free end of the opening extension 1200. When in use, the user can easily and smoothly remove the pluck end 1243 of the paper sealing cover 124 with the fingers of one hand, or hold the paper container 120 with one hand and use the fingers of the other hand to easily and smoothly remove the pluck end 1243 of the paper sealing cover 124, so that the inner locking protrusion 1241 and the cover eaves 1240 can leave the end of the opening extension 1200 to open the paper sealing cover 124. Then the paper fragrance capsule 12 is placed in an aroma diffuser, and the fragrance substance (such as scented wax, essential oil or spice) in the fragrance carrier 122 can be heated to generate aroma, and the aroma of the fragrance carrier 122 can be distributed into the air through the ventilation function of the breathable film 126.

When producing fragrance capsules, the producer worker can quickly combine the paper sealing cover 124 with the opening extension 1200 of the paper container 120 with one hand, and the hand of the producer will feel the vibration of the inner locking protrusion 1241 buckling the free end of the paper container opening extension 1200 to confirm that the paper sealing cover 124 is combined with the opening extension 1200 of the paper container 120. It is different from the conventional metal or plastic sealing sheet that is attached or thermally fused to the opening of the fragrance container, which requires more man-hours and costs. The paper sealing cover 124 can temporarily cover the paper container 120 when the paper fragrance capsule 12 is suspended for heating. The fragrance carrier 122 is sealed in the sealing cover 124 of the paper container 120, which can maintain the quality of the fragrance substance, prevent the fragrance substance from contacting with the outside air, and facilitate transportation or storage.

Please refer to FIG. 1, in one embodiment of the present invention, the paper container 120 is directly filled with a fragrance substance, including, for example, liquid or solid fragrance substance such as scented wax or essential oil, etc., which can be the same as the fragrance substances in the foregoing embodiments and will not be described in detail. In this implementation, no fragrance carrier is used to preserve the fragrance substance. The storage time of the fragrance substance inside the paper fragrance capsule 12 may be relatively short, but it is more economical. Its working performance and effect can refer to the foregoing embodiments. The paper fragrance capsule with breathable film comprises: a paper container 120, a fragrance substance 122, and a breathable film 126. The paper container 120 comprises an opening extension 1200, and a first coating 1201 bonded to the inner side of the paper container 120 and the opening extension 1200. The breathable film 126 comprises a tensile fixing layer 1261 and a microporous film 1262. The tensile fixing layer 1261 has first pores 1263. The microporous film 1262 has second pores 1264. The tensile fixing layer 1261 is combined with the microporous film 1262 to form the breathable film 126. The pore diameter of the first pores 1263 is larger than that of the second pores 1264.

The fragrance substance 122 is placed in the paper container 120. The peripheral edge of the breathable film 126 is combined with the opening extension 1200 and covered on the fragrance substance 122, and the breathable film 126 has waterproof and breathable functions.

Please refer to FIG. 2 and FIG. 3, in one embodiment of the present invention, the paper container 120 also comprises a third coating 1203 combined on the outer side of the paper container 120. The material of the third coating 1203 is the same as the above coating material. The third coating 1203 is used to prevent external oil, water, moisture and other external pollutants from corroding or penetrating the paper container 120. On the other hand, if the paper fragrance capsule 12 or the fragrance carrier 122 is filled with various liquid fragrance substances, especially some relatively volatile fragrance substances, the volatile fragrance substances may be partially exposed to the adsorption and evaporation process, causing penetration or contamination to the first coating 1201 and the inner wall of the paper container 120. The third coating 1203 can prevent internal oil, water, moisture, etc. from eroding or penetrating into the outer environment of the paper container 120.

What the invention claimed is:

1. A paper fragrance capsule with breathable film, comprising: a paper container, a fragrance carrier and a breathable film, wherein:
    said paper container comprises an opening extension, and a first coating coated on an inner side of said paper container and said opening extension;
    said fragrance carrier is placed in the paper container, said fragrance carrier comprising a plurality of third pores filled with a fragrance substance inside;
    said breathable film is waterproof and breathable and covered on said fragrance carrier with a peripheral edge thereof combined with said opening extension, said breathable film comprising a tensile fixing layer and a microporous film, said tensile fixing layer comprising a plurality of first pores, said microporous film comprising a plurality of second pores, said tensile fixing layer combining with said microporous film to form said breathable film, the pore diameter of said first pores being larger than the pore diameter of said second pores.

2. The paper fragrance capsule with breathable film as claimed in claim 1, wherein said first coating comprising PE, PP, PLA, CPE, PET, LDPE, HDPE, LLDPE and Propylene ethylene.

3. The paper fragrance capsule with breathable film as claimed in claim 1, wherein the material of said microporous film comprises TPE, TPU, PE, polytetrafluoroethylene (PTFE), polyolefin, PU or precipitated polyurethane; said tensile fixing layer is a mesh structure film, which combines tensile materials with a network-like elongated film on one side of said microporous film, forming said tensile fixing layer of said mesh structure film as a fixed support for said microporous film.

4. The paper fragrance capsule with breathable film as claimed in claim 3, wherein the material of said mesh structure film forming said tensile fixing layer includes fiber, carbon fiber, glass fiber, polyester fiber, nylon, PP, plastic or metal.

5. The paper fragrance capsule with breathable film as claimed in claim 1, wherein the material of said microporous film comprises TPE, TPU, PE, polytetrafluoroethylene (PTFE), polyolefin, PU or precipitated polyurethane; the material of said tensile fixing layer is a tensile fixing layer formed by a fiber fixing film, which has at least two layers of fibers interweaving irregularly and stacked to form a plurality of said first pores.

6. The paper fragrance capsule with breathable film as claimed in claim 1, wherein said microporous film has an upper side thereof combined with said tensile fixing layer to form said breathable film, and the peripheral edge of said microporous film is combined with the part of said first coating part on said opening extension.

7. The paper fragrance capsule with breathable film as claimed in claim 1, wherein said microporous film has a lower side thereof combined with said tensile fixing layer to form said breathable film, and the peripheral edge of said tensile fixing layer is combined with the part of said first coating part on said opening extension.

8. The paper fragrance capsule with breathable film as claimed in claim 1, further comprising a paper sealing cover, said paper sealing cover comprising a cover eaves extending downwards from the periphery thereof, an inner locking protrusion located on an inner side of said cover eaves and a pluck end protruding outward from said inner locking protrusion, said paper sealing cover being incorporated with said opening extension, said inner locking protrusion being used to releasably engage with the free end of said opening extension.

9. The paper fragrance capsule with breathable film as claimed in claim 8, wherein said paper sealing cover further comprises a layer of second coating combined on an inner side thereof.

10. The paper fragrance capsule with breathable film as claimed in claim 1, wherein the material of said fragrance carrier is selected from the group of absorbent body, sponge, foam, open-pore sponge, porous ceramics, plaster, wood, cloth, fiber cloth, paper and porous rubber.

11. The paper fragrance capsule with breathable film as claimed in claim 1, wherein the surface of said paper container and/or said paper sealing cover is formed with a rough coefficient surface.

12. The paper fragrance capsule with breathable film as claimed in claim 1, wherein said paper container further comprises a third coating coated on an outer side thereof.

* * * * *